US010286229B2

(12) United States Patent
Baltes et al.

(10) Patent No.: US 10,286,229 B2
(45) Date of Patent: *May 14, 2019

(54) SYSTEMS, METHODS, AND DEVICES FOR REAL-TIME TREATMENT VERIFICATION USING AN ELECTRONIC PORTAL IMAGING DEVICE

(71) Applicants: VARIAN MEDICAL SYSTEMS, INC., Palo Alto, CA (US); VARIAN MEDICAL SYSTEMS INTERNATIONAL AG, Zug (CH)

(72) Inventors: Christof Baltes, Oberwil-Lieli (CH); Todd Holmes, Bethlehem, PA (US)

(73) Assignees: VARIAN MEDICAL SYSTEMS, INC., Palo Alto, CA (US); VARIAN MEDICAL SYSTEMS INTERNATIONAL AG, Zug (CH)

( * ) Notice: Subject to any disclaimer, the term of this patent is extended or adjusted under 35 U.S.C. 154(b) by 453 days.

This patent is subject to a terminal disclaimer.

(21) Appl. No.: 15/002,526

(22) Filed: Jan. 21, 2016

(65) Prior Publication Data

US 2016/0136460 A1    May 19, 2016

Related U.S. Application Data

(63) Continuation of application No. 14/175,492, filed on Feb. 7, 2014, now Pat. No. 9,265,971.

(51) Int. Cl.
*A61B 6/00* (2006.01)
*A61N 5/10* (2006.01)

(52) U.S. Cl.
CPC .............. *A61N 5/1071* (2013.01); *A61B 6/42* (2013.01); *A61B 6/4258* (2013.01); *A61B 6/486* (2013.01);

(Continued)

(58) Field of Classification Search
CPC ......... A61B 6/42; A61B 6/4258; A61B 6/486; A61B 6/52; A61B 6/5205;

(Continued)

(56) References Cited

U.S. PATENT DOCUMENTS 8,130,905 B1    3/2012  Nelms
8,351,572 B1    1/2013  Renner (Continued)

FOREIGN PATENT DOCUMENTS

| CN | 101015723 A | 8/2007 |
|---|---|---|
| WO | WO 2011/098891 A1 | 8/2011 |
| WO | WO 2012/088321 A1 | 6/2012 |

OTHER PUBLICATIONS

Berbeco et al., "Clinical Feasibility of Using an EPID in Cine Mode for Image-Guided Verification of Stereotactic Body Radiotherapy," *Int. J. Radiation Oncology Biol. Phys.*, 2007, 69(1): pp. 258-266.

(Continued)

*Primary Examiner* — Chih-Cheng Kao
(74) *Attorney, Agent, or Firm* — Shapiro, Gabor and Rosenberger, PLLC (57) ABSTRACT

A radiation dose received by a patient from a radiation therapy system can be verified by acquiring a cine stream of image frames from an electronic portal imaging device (EPID) that is arranged to detect radiation exiting the patient during irradiation. The cine stream of EPID image frames can be processed in real-time to form exit images providing absolute dose measurements at the EPID (dose-to-water values), which is representative of the characteristics of the radiation received by the patient. Compliance with predetermined characteristics for the field can be determined during treatment by periodically comparing the absolute dose measurements with the predetermined characteristics, which can include a predicted total dose in the field after full treatment and/or a complete irradiation area outline (CIAO).

(Continued)

The system operator can be alerted or the irradiation automatically stopped when non-compliance is detected.

29 Claims, 7 Drawing Sheets (52) U.S. Cl.
CPC .............. *A61B 6/52* (2013.01); *A61B 6/5205* (2013.01); *A61N 5/1031* (2013.01); *A61N 5/1045* (2013.01); *A61N 5/1048* (2013.01); *A61N 5/1067* (2013.01); *A61N 5/1047* (2013.01); *A61N 5/1075* (2013.01); *A61N 2005/1054* (2013.01)

(58) Field of Classification Search
CPC .......... A61N 2005/1054; A61N 5/1031; A61N 5/1045; A61N 5/1047; A61N 5/1048; A61N 5/1067; A61N 5/1071; A61N 5/1075
See application file for complete search history.

(56) References Cited

U.S. PATENT DOCUMENTS

| | | | |
|---|---|---|---|
| 8,605,857 | B1 | 12/2013 | Renner |
| 9,265,971 | B2 * | 2/2016 | Baltes .................. A61N 5/1071 |
| 2008/0002811 | A1 * | 1/2008 | Allison .................. A61N 5/103 378/65 |

OTHER PUBLICATIONS

Berry, Sean L., "Transit Dosimetry for Patient Treatment Verification with an Electronic Portal Imaging Device," PhD dissertation, Department of Applied Physics and Applied Mathematics, Columbia University, 2012.

Elmpt et al., "A literature review of electronic portal imaging for radiotherapy dosimetry," *Radiotherapy and Oncology*, 2008, 88: pp. 289-309.

Esch et al., "The use of an aSi-based EPID for routine absolute dosimetric pre-treatment verification of dynamic IMRT fields," *Radiotherapy & Oncology*, 2004, 71:pp. 223-234.

Fuangrod et al., "A system for EPID-based real-time treatment delivery verification during dynamic IMRT treatment," *Medical Physics*, Sep. 2013, 40(9): pp. 091907-1 to 091907-11.

Fuangrod et al., "Development of EPID-based Real time Dose Verification for Dynamic IMRT," *World Academy of Science, Engineering, and Technology*, 2011, 56:pp. 609-612.

Nicolini et al., "GLAaS: An absolute dose calibration algorithm for an amorphous silicon portal imager. Applications to IMRT verifications," *Medical Physics*, Aug. 2006, 33(8): pp. 2839-2851.

Nijsten et al., "A global calibration model for a-Si EPIDs used for transit dosimetry," *Medical Physics*, Oct. 2007, 34(10): pp. 3872-3884.

Rowshanfarzad et al., "Measurement and modeling of the effect of support arm backscatter on dosimetry with a Varian EPID," *Medical Physics*, May 2010, 37(5): pp. 2269-2278.

White paper entitled "Exit-Transit Dose Reconstruction Option in Dosimetry Check" [online]. Math Resolutions LLC, 2012 [retrieved on Feb. 7, 2014]. Retrieved from the Internet: <URL: http://www.mathresolutions.com/ExitWhitePaper.htm>.

Extended European Search Report, dated May 29, 2015, for European Application No. 15152628.2.

Vial et al. "A new concept in detector design for radiation therapy: Simultaneous imaging and dosimetry for comprehensive treatment verification," Nov. 2, 2013, Proceedings of the 2013 IEEE (NSS/MIC) Medical Imaging Conference, pp. 1-6.

Xu Shouping, "The Study of Patient Dose Verification Using the Electronic Portal Imaging Device," Chinese excellent master's degree thesis full text database English translation, Issue 3, 2016, E055-9.

Daniel A. Low, et al., "A Technique for the Quantitative Evaluation of Dose Distributions," Medical Physics, vol. 25, No. 5, May 1998, pp: 656-661.

Office Action dated Dec. 4, 2017, in Chinese Application No. 201510065212.2.

Office Action dated Aug. 8, 2018, in Chinese Patent Application No. 201510065212.2.

Office Action dated Mar. 4, 2019, in Chinese Patent Application No. 201510065212.2.

\* cited by examiner

SYSTEMS, METHODS, AND DEVICES FOR REAL-TIME TREATMENT VERIFICATION USING AN ELECTRONIC PORTAL IMAGING DEVICE

FIELD

The present disclosure relates generally to delivering radiation to a patient, and, more particularly, to systems, methods, and devices for real-time dosimetric verification of radiation therapy treatments using an electronic portal imaging device (EPTD).

BACKGROUND

Dynamic radiation treatment techniques, such as intensity-modulated radiation therapy (IMRT) and volumetric modulated arc therapy (VMAT), are typically used with a radiotherapy system, such as a linear accelerator (linac), equipped with a multi-leaf collimator (MLC) to treat pathological anatomies (tumors, lesions, vascular malformations, nerve disorders, etc.) by delivering prescribed doses of radiation (X-rays, gamma rays, electrons, protons, and/or ions) to the pathological anatomy while minimizing radiation exposure to the surrounding tissue and critical anatomical structures. Use of the MLC allows the radiotherapist to treat a patient from multiple angles while varying the shape and dose of the radiation beam, thereby providing a greatly enhanced ability to deliver radiation to a target within a treatment volume while avoiding excess irradiation of nearby healthy tissue. IMRT and VMAT, which are complex techniques involving the synchronous occurrence of gantry rotation, MLC motion, and dose rate modulation, are rapidly growing as radiation therapy techniques due to their ability to quickly deliver highly conformal dose distributions.

Quality assurance is an integral component in the workflow of clinical radiotherapy. After creating a clinical treatment plan, the performance of the different machine components to deliver the intended plan is checked in a pre-treatment verification step, which confirms that the treatment system is capable of delivering the intended dose distribution using the installed collimation devices, e.g., jaws or MLC. Different measurement methods can be applied, such as ion chamber or diode arrays that directly measure the delivered dose distribution without the patient in the beam and before the first treatment.

Recently, errors in the delivery of a radiation therapy have resulted in injury to patients, some with fatal consequences, despite pre-treatment verification. In particular, because this verification occurs without the patient in place, it cannot account for changes in setup, such as system errors or misalignment, that may inadvertently expose the patient to harmful radiation during treatment. Moreover, dose to the patient can be affected by significant changes in patient anatomy, such as weight loss or significant tumor shrinkage. Thus, a need exists for monitoring dose delivery during treatment of the patient, to account for potential errors, such as missing beam limiting devices, patient positioning errors, mismatch between treatment plan and patient, etc. and to account for anatomical changes.

SUMMARY

Systems, methods, and devices for real-time dosimetric verification of radiation therapy treatments using an electronic portal imaging device (EPID) are disclosed herein. The EPID of a radiation therapy system can be extended behind the patient. Radiation from the treatment system that exits the patient can be detected by the EPID, which generates a cine stream of megavoltage (MV) image frames. Based on these image frames and the resulting images, absolute dose (dose-to-water) of radiation received by the EPID can be calculated. These absolute dose values can be compared in real-time against pre-determined dose distribution characteristics. The comparison can include a check for radiation outside a boundary of the field at the onset of the treatment and/or an ongoing check for cumulative radiation dose that exceeds a total dose to be received by the patient for the entire treatment field. An error signal can be generated if the applied radiation field fails to conform to the intended dose profile. Thus, dose delivery during treatment can be monitored in real-time in order to prevent injury to the patient.

In embodiments, a method for verifying radiation dose received by a patient from a radiation therapy system can include irradiating a field using a radiation beam from the radiation therapy system. During the irradiating, a continuous stream (i.e., cine stream) of image frames can be acquired from an EPID that is arranged to detect radiation exiting the patient, and the cine stream of EPID image frames can be processed in real-time (e.g., by accumulating image frames over a predetermined time period to form respective exit images) in order to obtain dose measurements for the field as absolute dose-to-water values. In addition, during the irradiating, compliance with predetermined characteristics can be determined for the field by comparing the processed images with the predetermined characteristics. An error signal can be generated in response to a determination of non-compliance based on the comparing.

In embodiments, the predetermined characteristics can include a predicted total dose in the field after the full treatment, and the comparing can include a difference comparison between the absolute dose measurement and the predicted total dose. In embodiments, the predetermined characteristics can include a complete irradiation area outline (CIAO) of the field and the comparing can include a geometric comparison between the absolute dose measurements and the CIAO.

In embodiments, the acquired EPID images can be analyzed by performing at least one of a 2-D dose difference analysis and a gamma analysis. An error signal can be generated in response to a determination of at least one of an underdose, an overdose, or a dose outside of CIAO based on the further analyzing.

In embodiments, a system can include a real-time verification device. The real-time verification device can be configured to receive a continuous stream of exit EPID image frames and to process in real-time the continuous stream of image frames (e.g., by accumulating image frames over a predetermined time period to form respective exit images) in order to obtain absolute dose measurements at the EPID in a field of a radiation therapy as dose-to-water values. The verification device can be further configured to analyze the dose measurements with respect to predetermined characteristics for the field and to generate an error signal if the dose measurements are not compliant with one or more of the predetermined characteristics.

In embodiments, the system can include the verification device, an EPID configured to generate a continuous stream of image frames, and a radiation therapy system with a source that generates a radiation beam for irradiating the patient in performing the radiation therapy, wherein the verification device is configured to analyze the dose measurements in real-time during irradiation of the patient.

In embodiments, a non-transitory computer-readable medium can be provided in combination with a computer processing system to perform embodiments of the disclosed methods. The non-transitory computer-readable storage medium can be embodied with a sequence of programmed instructions for verifying radiation dose received at an EPID from a radiation therapy system. The computer processing system can execute the sequence of programmed instructions embodied on the computer-readable storage medium to cause the computer processing system to perform the method steps.

Objects and advantages of embodiments of the disclosed subject matter will become apparent from the following description when considered in conjunction with the accompanying drawings.

BRIEF DESCRIPTION OF DRAWINGS

Embodiments will hereinafter be described with reference to the accompanying drawings, which have not necessarily been drawn to scale. These drawings are for illustration purposes only and are not intended to limit the scope of the present disclosure in any way. Where applicable, some features may not be illustrated to assist in the illustration and description of underlying features. Throughout the figures, like reference numerals denote like elements. As used herein, various embodiments can mean one, some, or all embodiments.

DETAILED DESCRIPTION

An electronic portal imaging device (EPID) can be used to verify the correct treatment of a patient by measuring the radiation that passes through the patient and is thus incident on the EPID (i.e., an exit image). A cine stream of exit image frames taken during patient treatment is processed and used to verify, in real-time or near real-time (e.g., less than one second), that the dose as delivered is not harmful to the patient. As used herein, cine stream refers to a continuous stream of image frames acquired by the EPID during a continuous acquisition mode of operation.

For example, the EPID can run at a particular frame rate, such as but not limited to 15 frames per second, which rate may be a configurable setting that optimizes, among other things, imaging capabilities subject to EPID or other hardware limitations. Image frames acquired over a predetermined time period for dosage check can be combined together (e.g., by summing) to form a single exit image, which may represent the dose reaching the EPID over that time period. For example, in embodiments, the predetermined time period is 1 second and the number of image frames summed together to form a single exit image is 15. In embodiments, the predetermined time period is 5 seconds and the number of image frames summed together to form a single exit image is 75. Of course, other frame rates and accumulating time periods are also possible according to one or more contemplated embodiments. For example, the time period may be less than one second or greater than five seconds. Moreover, the frame rate may be constant (e.g., about 15 image frames per second) or variable during a treatment.

The EPID images provide absolute dose values (i.e., dose-to-water, cGy) for the radiation received at the EPID, which eliminates potential inaccuracies that are associated with other types of dose calculations. If the radiation dose is determined to be non-conforming, and thus potentially harmful to the patient, an error signal can be triggered. The error signal can alert the operator and/or automatically halt irradiation of the patient.

Figure 1:
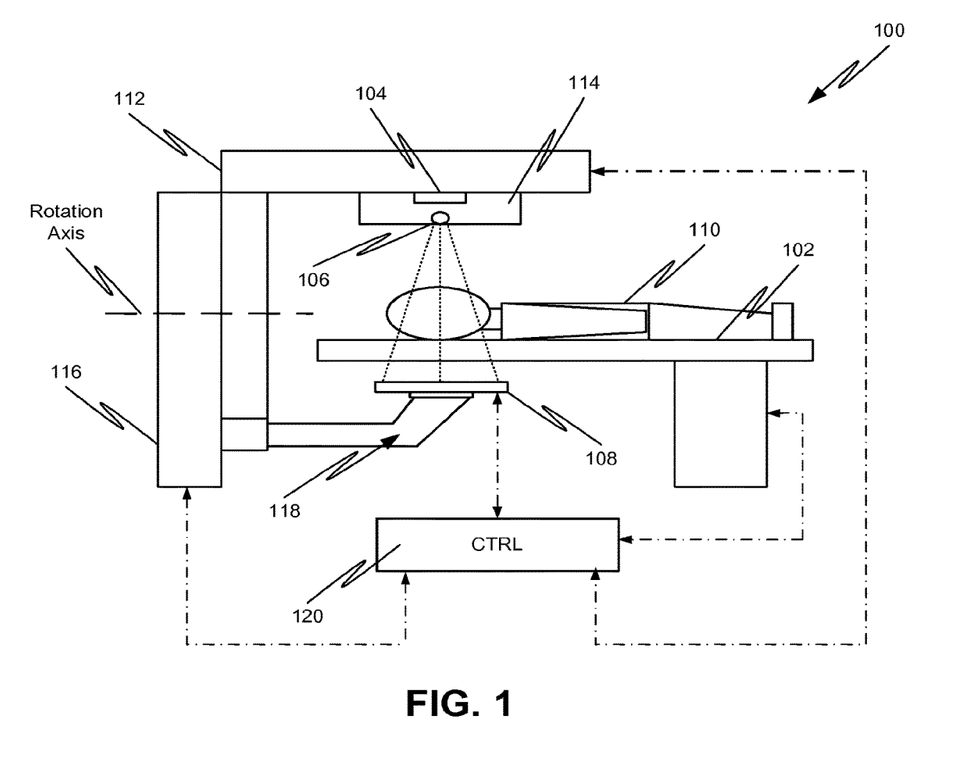
FIG. 1 shows features of a radiation therapy system for irradiating a patient, according to various embodiments of the disclosed subject matter.

Referring to FIG. 1, an exemplary radiation therapy treatment system 100 is shown. The treatment system 100 can provide radiation therapy to a patient 110 positioned on a treatment couch 102 and can allow for the implementation of various real-time radiation dose verification protocols. The radiation therapy treatment can include photon-based radiation therapy, particle therapy, electron beam therapy, or any other type of treatment therapy.

In an embodiment, the radiation therapy treatment system 100 includes a radiation treatment device 116, such as, but not limited to, a radiotherapy or radiosurgery device, which has a gantry 112 supporting a radiation module 114 with one or more radiation sources 106 and a linear accelerator (linac) 104 operable to generate a beam of kilovolt (kV) or megavolt (MV) X-ray radiation. The gantry 112 can be a ring gantry (i.e., it extends through a full 360° arc to create a complete ring or circle), but other types of mounting arrangements may also be employed. For example, a static beam, or a C-type, partial ring gantry, or robotic arm can be used. Any other framework capable of positioning the radiation module 114 at various rotational and/or axial positions relative to the patient 110 may also be used.

The radiation module 114 can also include a modulation device (not shown) operable to modulate the radiation beam as well as to direct the therapeutic radiation beam toward the patient 110 and a portion thereof that is to be irradiated. The portion desired to be irradiated is referred to as the target or target region or a region of interest. The patient 110 may have one or more regions of interest that need to be irradiated. A collimation device (not shown) may be included in the modulation device to define and adjust the size of an aperture through which the radiation beam passes from source 106 to patient 110. The collimation device can be controlled by an actuator (not shown), which can be controlled by controller 120.

In an embodiment, the radiation therapy device is a kV or MV energy intensity modulated radiotherapy (IMRT) device. The intensity profiles in such a system are tailored to the treatment requirements of the individual patient. The IMRT fields are delivered with a multi-leaf collimator (MLC), which can be a computer-controlled mechanical beam shaping device attached to the head of the linac 104 and includes an assembly of metal fingers or leaves. The MLC can be made of 120 movable leaves with 0.5 cm and/or 1.0 cm leaf width, for example. For each beam direction, the optimized intensity profile is realized by sequential delivery of various subfields with optimized shapes and weights. From one subfield to the next, the leaves may move with the radiation beam on (i.e., dynamic multi-leaf collimation (DMLC)) or with the radiation beam off (i.e., segmented multi-leaf collimation (SMLC)). The device 116 can also be a tomotherapy device where intensity modulation is achieved with a binary collimator which opens and closes under computer control. As the gantry continuously rotates around the patient, the exposure time of a small width of the beam can be adjusted with opening and closing of the binary collimator, allowing radiation to be delivered to the tumor through the most desirable directions and locations of the patient.

Alternatively, the device 116 can be a helical tomotherapy device, which includes a slip-ring rotating gantry or an intensity modulated arc therapy device (IMAT), which uses rotational cone beams of varying shapes to achieve intensity modulation instead of rotating fan beams. In still another alternative, the device 116 can be a simplified intensity modulated arc therapy (SIMAT) device which uses multiple arcs, or a sweeping window arc therapy device (SWAT), which sweeps the MLC leaf positions across the target planning volume (TPV) with rotation. In yet another alternative, the device 116 can be a volumetric modulated arc therapy (VMAT) device where dose rate, beam aperture shape, and the speed of rotation can be continuously varied to deliver the prescribed dose to the TPV. Indeed, any type of IMRT device can be employed as treatment device 116. For example, embodiments of the disclosed subject matter can be applied to image-guided radiation therapy (IGRT) devices. Each type of device 116 can be accompanied by a corresponding radiation plan and radiation delivery procedure.

Device 116 can include a portal dose imaging device 118 for acquiring digital images to be used for portal dosimetry verification. The portal dose imaging device 118 can include EPID 108. The portal dose imaging device 118 can be placed at different locations, such as, on top of the treatment couch 102, or attached to the accelerator head 104, for example. The portal dose imaging device 118 can generate immediate 2-D digital information. For example, the imaging device 118 can include a camera-based device. The EPID 108 can also be a CCD-camera based device, which includes, in effect, an array of simultaneously integrating dosimeters with a dead time in between acquired frames of about 0.1 ms, for example. Another alternative is a flat panel imager, or amorphous silicon EPID, which offers good image quality, high optical transfer efficiency, large imaging area, and resistance to radiation.

An exemplary amorphous silicon EPID that can be used in embodiments is the Varian aS1000 or the Varian aS500 (both sold by Varian Medical Systems, Palo Alto, Calif.). Optionally, the EPID can include backscatter shielding, which may assist in the calculation of absolute dose measurements at the EPID. However, EPIDs that do not use backscatter shielding can also be employed. Any effect of backscatter on absolute dose calculation when using EPIDs without such shielding can be mitigated or removed via image processing, for example, by using the method described in the publication entitled "Measurement and modeling of the effect of support arm backscatter on dosimetry with a Varian EPID," (published in *Medical Physics*, May 2010, 37(5): pp. 2269-78), which is incorporated by reference herein.

In general, EPID 108 has picture elements (pixels) that register the amount of radiation that falls thereon and convert the received amount of radiation into a corresponding number of electrons. The electrons are converted into electrical signals which are further processed using either the imaging device 118 or controller 120. Such a configuration (i.e., digital imaging detector(s) positioned opposite the therapeutic source(s) with the patient therebetween) provides the ability to continuously and immediately capture the energy and intensity of the therapeutic radiation exiting the patient, in order to generate two-dimensional (2-D) exit images of digitized X-ray measurements. Because the portal dose imaging device 118 generates immediate, 2-D digital information, it facilitates 2-D dosimetry at any gantry angle. Thus, the techniques described above and elsewhere herein are applicable to static arc treatments as well as continuous arc and other beam deliveries.

The controller 120 can include a computer with typical hardware such as a processor, and an operating system for running various software programs and/or communication applications. The computer can include software programs that operate to communicate with the radiation therapy device 116, which software programs are operable to receive data from external software programs and hardware. The computer can also include any suitable input/output devices adapted to be accessed by medical personnel, as well as input/output (I/O) interfaces, storage devices, memory, keyboard, mouse, monitor, printers, scanner, etc. The computer can also be networked with other computers and radiation therapy systems. Both the radiation therapy device 116 and the controller 120 can communicate with a network as well as a database and servers. The controller 120 can be configured to transfer medical image related data between different pieces of medical equipment.

The system 100 can also include a plurality of modules containing programmed instructions (e.g., as part of controller 120, or as separate modules within system 100, or integrated into other components of system 100), which instructions cause system 100 to perform different functions related to radiation therapy/surgery, as discussed herein, when executed. For example, system 100 can include image processing and evaluation modules that provide real-time verification of the absolute dose at the EPID during irradiation. The system can also include a portal dosimetry module that provides post-treatment verification of intended radiation dose, including a 2-D map of underdose and overdose conditions.

The dosage measurements provided by the system 100 can be in absolute dose values (i.e., dose-to-water) at the EPID. Although the actual dose received by the patient is not calculated, the absolute dose at the EPID is representative of the dose conditions received by the patient since the radiation received at the EPID should have passed through the patient. Prior to treatment, the absolute dose measured by the EPID (i.e., at the plane of the EPID) is predicted. If the absolute dose actually measured by the EPID matches the predicted dose, then the conditions underlying the prediction can be presumed to match the actual treatment conditions. Thus, dose delivery to the patient, patient anatomy, and/or patient setup can be in compliance with the original treatment plan. However, noncompliance of the absolute dose measurements at the EPID as compared to the predicted dose can be indicative of some error in radiation delivery to the patient, such as deviations of patient anatomy or setup from the treatment plan or an erroneous radiation therapy device configuration.

The system 100 can further include a treatment delivery module operable to instruct the radiation therapy device 116 to deliver the treatment plan with or without the patient 110 in place, an image processing module operable to receive the cine stream of EPID image frames and to process the image frames into 2-D portal images and absolute dose values, and a real-time evaluation module operable to compute comparisons between predicted and measured absolute dose distributions and to calculate radiation delivery errors. The modules can be written in C or C++ programming languages, for example. Computer program code for carrying out operations as described herein may also be written in other programming languages.

Figure 2:
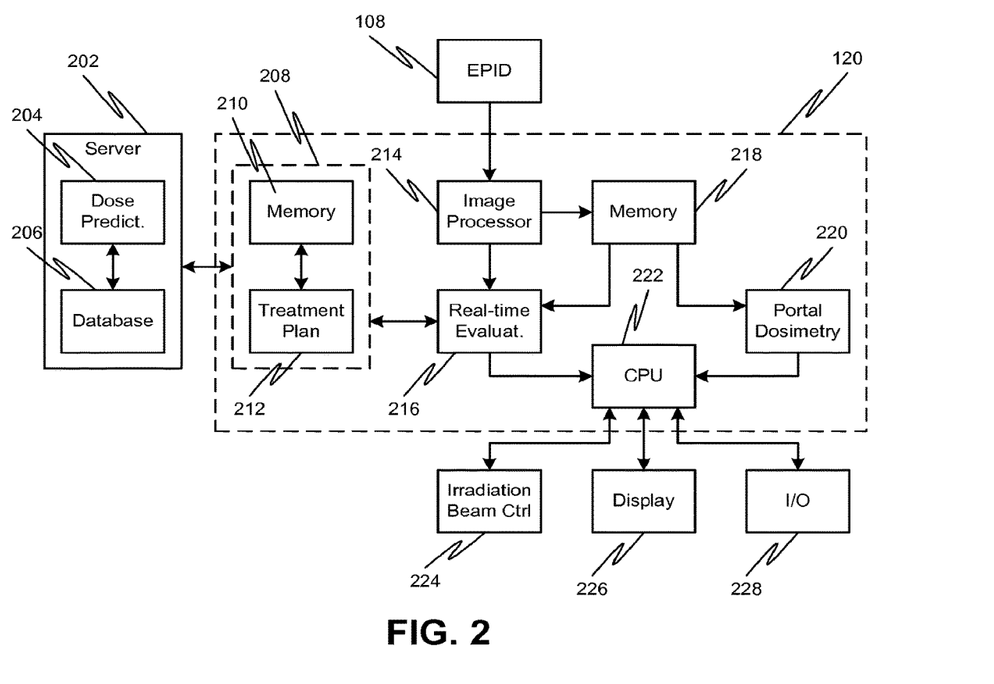
FIG. 2 shows features of a control system for real-time dose verification, according to various embodiments of the disclosed subject matter.

Referring to FIG. 2, a controller 120 can include one or modules for operating the radiation therapy system, for example, via irradiation beam controller 224 and for processing the cine stream of image frames from EPID 108. As noted above, the processing of the cine stream can include accumulating image frames obtained over a set period of time into a single exit image. The controller 120 can communicate with a server 202, for example, a remote server, which can include a database 206 in communication with a dose prediction module 204. The dose prediction module 204 can predict various features of the radiation dose for a specific treatment modality, such as absolute dose distributions (dose-to-water) at the EPID in each treatment field. For example, the dose prediction module 204 can be an Eclipse™ treatment planning system and the database 206 can be part of an ARIA® oncology information system (both sold by Varian Medical Systems, Palo Alto, Calif.).

Information regarding the predicted absolute dose distributions can be communicated from server 202 to controller 120, and in particular, the treatment console 208 of controller 120. Alternatively or additionally, absolute dose distributions can be predicted using treatment planning module 212 of treatment console 208. Treatment planning module 212 may also determine a desired treatment plan for irradiating a patient for a particular treatment. The treatment plan can include radiation dosage information and beam shape for one or more control points necessary to effect a desired treatment of the patient. Treatment console 208 can also include, for example, a memory module 210 for storage of dose prediction information (e.g., predicted absolute dose information and/or predicted exit images for each field in a treatment plan) as well as treatment plan information.

A cine stream of image frames from EPID 108 can be received and processed by the controller 120, in particular, image processing module 214. An evaluation module 216 of the controller 120 can compare the absolute dose information to one or more characteristics of the predicted dose for the irradiation field, for example, from treatment console 208, to determine if any errors are present during treatment. Alternatively or additionally, processed images from the image processing module 214 can be stored in memory module 218. The evaluation module 216 can use information from stored images to determine cumulative dosage information, for example. Although memory module 218 and memory module 210 are shown separately, it is also possible to integrate modules 210 and 218 together as a single memory module, or to split the functions of modules 210 and 218 among more than two memory modules, according to one or more contemplated embodiments.

When the evaluation module 216 determines that an error exists, the evaluation module 216 can provide information regarding the error to processor 222, for example, a computer processing unit (CPU), which generates an error signal. The error signal can include information related to the type of error detected, such as irradiation dose outside of intended CIAO or that accumulated dose received by the patient exceeds the total dose for that particular field. The error signal from the processor 222 can communicate directly with an irradiation beam control unit, for example, to immediately interrupt beam irradiation of the patient to reduce the risk of injury to the patient. Alternatively or additionally, the error signal can be provided to a display 226, for indicating the presence and nature of the error to the treatment system operator. For example, the display 226 can illustrate the deviation of the radiation dose from predictions on one of the EPID exit images, such as indicating a region where the accumulated dose exceeds a total dose or where the dose is outside the CIAO. If the system operator determines that the error is a false alarm or otherwise will not negatively affect the patient's treatment, the operator may override the error using input/output module 228 and thereby allow treatment to continue.

After the field is completed, for example, immediately after termination of irradiation for that field, the EPID images stored in memory module 218 can be processed by portal dosimetry module 220. Portal dosimetry module 220 can perform a full portal dosimetry analysis on the acquired images, e.g., a more processing intensive 2-D analysis to determine regions of underdose, overdose, or other deviations in the radiation field. For example, the portal dosimetry module (as well as the various descriptions of portal dosimetry described herein) can be Varian's Portal Dosimetry product (sold by Varian Medical Systems, Palo Alto, Calif.). When the portal dosimetry module 220 determines that an error exists, it can provide information regarding the error to processor 222, which generates an error signal. The error signal can include information related to the type of error detected, such as underdose or overdose conditions for a region of the field. The error signal from the processor 222 can communicate directly with an irradiation beam control unit, for example, to provide an interlock that prevents further irradiation of the patient. Alternatively or additionally, the error signal can be provided to a display 226, for indicating the presence and the nature of the error to the treatment system operator. For example, the display 226 can illustrate regions of underdose or overdose on one of the EPID exit images. If the system operator determines that the error is a false alarm or otherwise will not negatively affect the patient's treatment, the operator may override the interlock using input/output module 228 in order to proceed with a subsequent radiation field.

Figure 3:
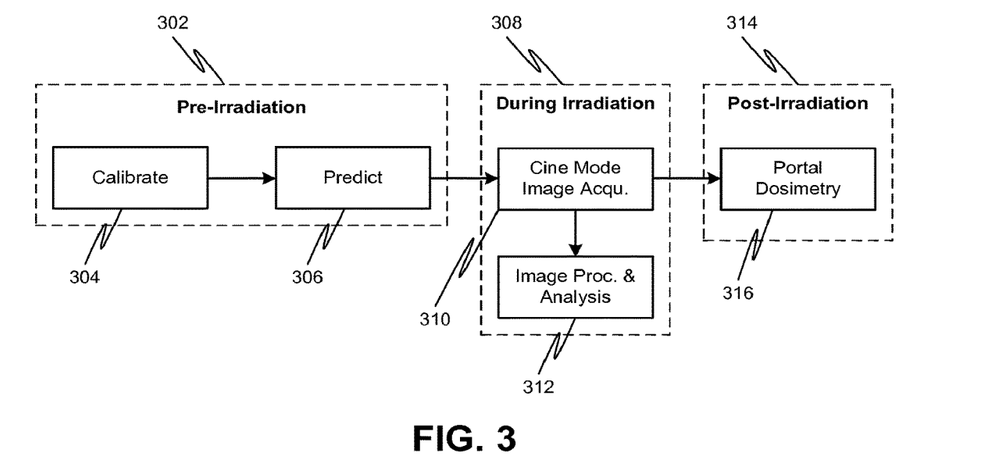
FIG. 3 shows features of dose verification at different stages of treatment, according to various embodiments of the disclosed subject matter.

FIG. 3 illustrates various high-level features of the disclosed dosimetric verification that can reduce the risk of injury to the patient. The dosimetric verification can include a pre-irradiation regimen 302, a regimen concurrent with irradiation 308, and a post-irradiation regimen 314. The pre-irradiation regimen 302 can include calibration 304 of the EPID, in particular, such that it produces absolute dose measurements (dose-to-water (cGy)) for all field geometries and at all points of the EPID. Such calibration techniques for producing absolute dose information from exit EPID images are known in the art, and one of ordinary skill in the art can readily produce such results based on, for example, the publication entitled, "A global calibration model for a-Si EPIDs used for transit dosimetry," (published in *Medical Physics*, October 2007, 34(10): pp. 3872-84), which is incorporated by reference herein.

The pre-irradiation regimen 302 can also include prediction 306. For example, the dose prediction module 204 can be used in prediction 306 to predict various features of the radiation dose for a specific treatment modality, such as absolute dose distributions (dose-to-water) at the EPID for each treatment field. Prediction 306 can also include configurations for one or more radiation fields, for example, to effect a desired radiation treatment. Information regarding calibration 304 and prediction 306 can be used during the irradiation regimen 308 to enable real-time dose verification.

During the irradiation regimen 308, the system can acquire image frames from the EPID in real-time, i.e., via a cine mode image acquisition 310, which can be performed, for example, by image processing module 214. The image acquisition 310 can also involve correction of the acquired image frames, for example, to account for positioning variations (e.g., positioning of the EPID) or backscatter. Subsequently, the image frames can be processed and analyzed, for example, by evaluation module 216, to form an exit image and to determine whether there are any errors in the irradiation dose. In particular, image processing and analysis regimen 312 can include converting the images to provide a measure of absolute dose (dose-to-water) at the EPID.

The image processing and analysis 312 can be configured to process the image frames and provide an evaluation in real-time or near real-time (e.g., less than one second). For example, the analysis 312 can involve the evaluation of absolute dose measurement to determine if the irradiation (or radiation exceeding a predetermined safe threshold) is outside the desired CIAO at the beginning of the treatment to avoid potential injury to healthy tissue of the patient. Such an initial analysis can provide an indication of major problems associated with the irradiation, for example, a missing MLC.

Alternatively or additionally, the analysis 312 can involve the evaluation of absolute dose measurements to determine if a cumulative dose received by the patient exceeds a total planned dose for the particular field. To this end, a difference calculation (i.e., determining if a dose exceeds a common maximum value at any point in the irradiation field) can be used, which reduces processing time and can allow for real-time (or near real-time) dose evaluation. Such an analysis can occur at regular intervals during irradiation (e.g., every five seconds after initiation of irradiation) and can detect less significant anomalies, for example, a stuck MLC leaf or a beam steering problem. Alternatively, such an analysis can be performed at regular intervals during radiation together with the above analysis with respect to the CIAO, either simultaneously or sequentially. By virtue of this real-time evaluation of absolute dose information, any damage that may result from improper irradiation of the patient can thus be minimized, or at least reduced.

The processed images can also be used in post-irradiation regimen 314. For example, images obtained from the EPID during irradiation (e.g., via cine mode image acquisition 310) can be employed in a full portal dosimetry analysis 316. The portal dosimetry analysis 316 can be performed, for example, by portal dosimetry module 220 of controller 120. Timing of the analysis is less of an issue to prevent immediate injury to the patient since irradiation has already been completed. Therefore, full portal dosimetry analysis 316 can involve more time-intensive processing to determine conditions of both underdose and overdose at each point in the CIAO. For example, difference and gamma processing can be employed to produce a full 2-D analysis of the measured absolute dose based on the exit images obtained by the EPID. If the analysis indicates that an error is present (e.g., conditions of overdose that may pose a risk of injury to the patient should radiation treatment continue), an interlock can be asserted to prevent further treatment (i.e., prevent proceeding to the next irradiation field), subject to override by a system operator.

Figure 4:
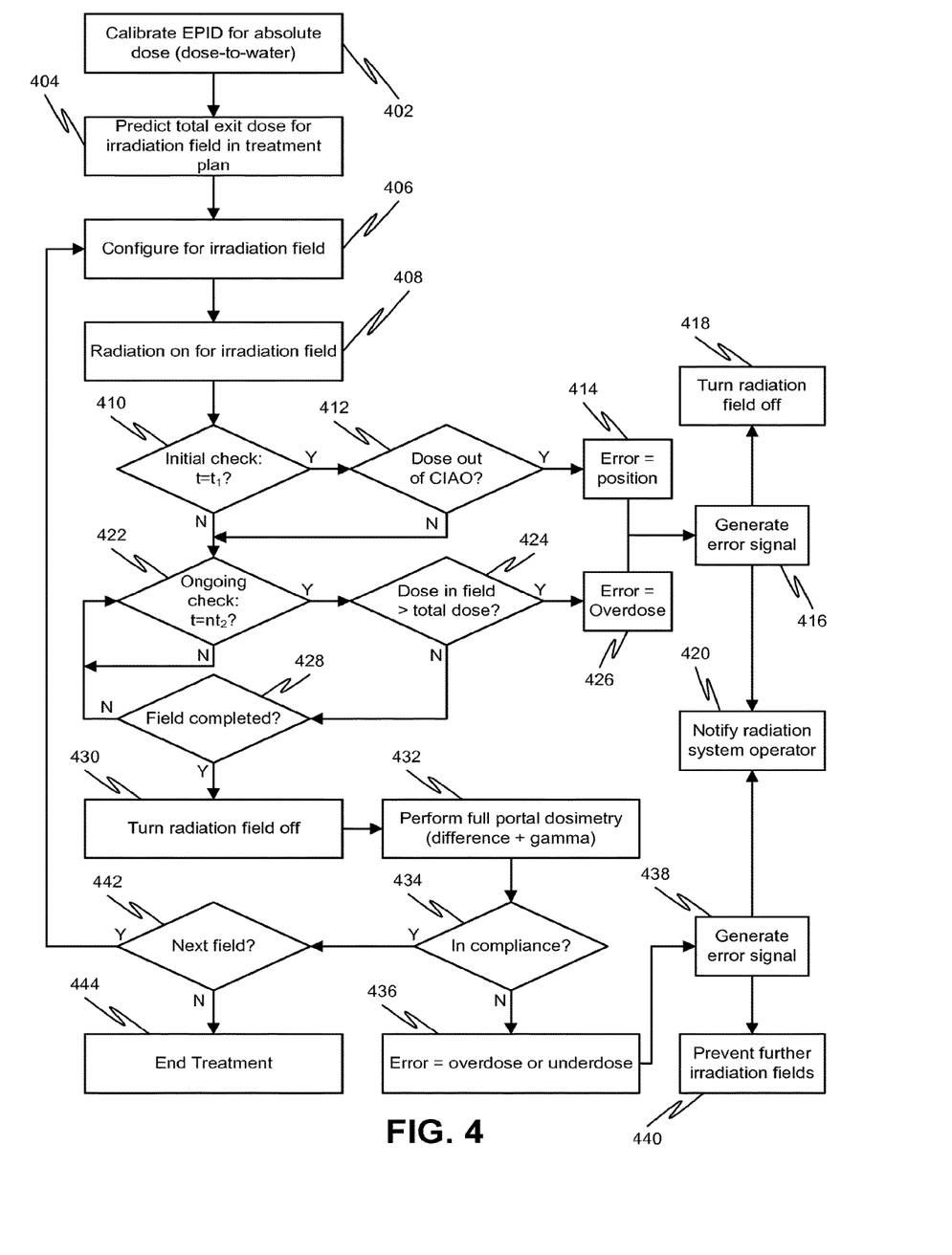
FIG. 4 is a process flow diagram of a dose verification method, according to various embodiments of the disclosed subject matter.

Referring to FIG. 4, a process flow diagram of an exemplary dosimetric verification method is shown. At 402, the EPID is calibrated to provide absolute dose measurements (dose-to-water) of the radiation at the EPID based on exit images obtained during irradiation of the patient. Calibration to provide absolute dose measurements can be performed as described in the incorporated by reference October 2007 publication noted above. At 404, a treatment plan can be generated that predicts the absolute dose values for each irradiation field. The geometry of the CIAO and the total absolute dose (i.e., the maximum cumulative dose for the irradiation field) are noted for dose verification during the irradiation.

At 406, the system can be configured for a particular irradiation field. For example, the patient can be positioned on the treatment couch. The EPID can then be extended and positioned with respect to the patient in order to detect an exit image, i.e., to detect radiation from the radiation system that has passed through the patient. The radiation system can then be configured for a particular irradiation field, for example, by positioning the MLC or beam steering components to provide a desired CIAO.

After configuration for the irradiation field is complete, the radiation beam is turned on at 408. An initial check of the irradiation field can be performed at 410. For example, at one second after the initiation of irradiation (i.e., when $t=t_1=1$ s), it is determined at 412 if the applied irradiation field complies with the desired CIAO for the field (i.e., geometry check). If radiation (or radiation exceeding a safe threshold) is received outside of the CIAO, it may damage healthy tissue or otherwise injure the patient. Thus, the initial check should be performed before any significant damage to the patient may occur. While it is unlikely that a sufficiently harmful dose will be delivered to the patient by errant field geometry during the first second after beam initiation, other time periods, either shorter or longer, for the initial evaluation are also possible according to one or more contemplated embodiments.

If the exit image analysis indicates that a dose is received outside of the CIAO, a determination of an error based on position or geometry is made at 414 and an error signal can be generated at 416. The error signal may result in automatic shut-off of the radiation field at 418 and/or notification to the radiation system operator of the error at 420. The notification to the radiation system operator at 420 can be in the form of a general error indication (e.g., visual or audio alarm, or on-screen pop-up notification, that an error exists), a specific error indication (e.g., description of the nature of the error), or a graphical error indication (e.g., a graphical representation on an exit image obtained by the EPID).

If the dose is determined to be compliant with the desired CIAO at 412, irradiation can continue subject to an ongoing evaluation for overdose. Such an evaluation may be performed periodically or continuously. Processing of the image frames for determination of cumulative absolute dose may be configured to occur in real-time or near-real time (e.g., less than one second). Should the cumulative dose at any point in time exceed the total dose planned for the treatment field, further irradiation beyond this point may result in harm to the patient. Thus, the ongoing check monitors the absolute dose received at the EPID (determined by the EPID exit images) in order to respond to conditions of potential overdose, for example, by terminating irradiation of a particular field earlier than anticipated.

The evaluation of the images may occur at discrete time periods to reduce the amount of processing involved without substantially increasing the risk of injury to the patient. For example, every five seconds after the initiation of irradiation (i.e., when $t=n \times t_2 = n \times 5$ s) as determined at 422, an evaluation of the cumulative dose with respect to a total dose for the irradiation field is performed at 424 (i.e., overdose check). However, other time periods, either shorter or longer, for the ongoing evaluation are also possible according to one or more contemplated embodiments. For example, there may be periods during treatment where irradiation is temporarily suspended, such as by gating or during beam-off periods due to patient motion or planned beam breaks in the treatment plan. Embodiments of the disclosed methods and systems can recognize and take advantage of such irradiation suspension events, for example, to process data to catch up on an evaluation of dose delivery compliance with a plan, especially if such evaluations are computationally intensive.

Figure 5:
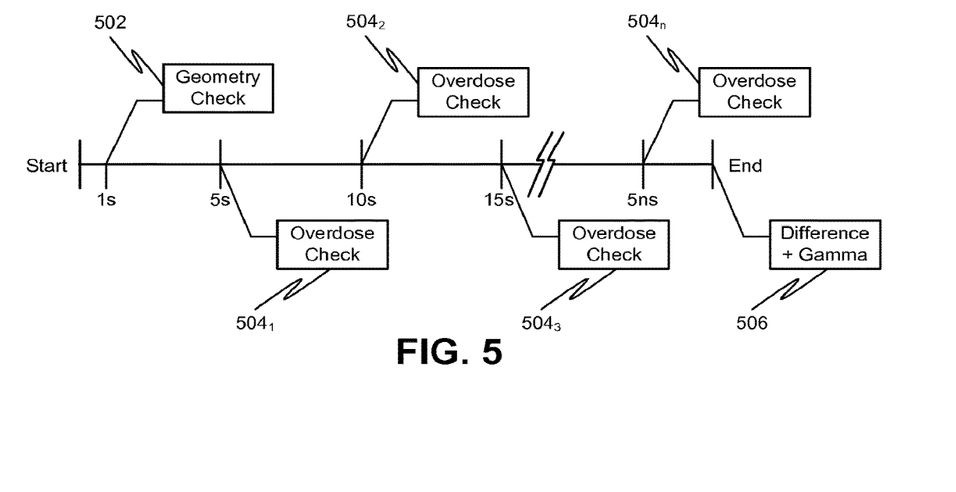
FIG. 5 shows exemplary timing of quality assurance checks during and after treatment, according to various embodiments of the disclosed subject matter.

FIG. 5 shows an exemplary time line for different dose verification analyses. For example, one second after initiation of irradiation for a particular field, a geometry check 502 that compares the irradiation field to the desired CIAO is performed (i.e., 412 in FIG. 4). If no errors are indicated or irradiation continues, then an overdose check $504_1$ can be performed at five seconds after initiation of irradiation for the particular field (i.e., 424 in FIG. 4). If no errors are indicated or irradiation continues, a second overdose check $504_2$ can be performed at ten seconds, a third overdose check $504_3$ can be performed at fifteen seconds, and additional overdose checks $504_n$ can be performed at each five second interval 5n until irradiation terminates. Such time periods for the geometry and overdose checks are merely exemplary and other time periods are also contemplated. The geometry and/or overdose checks can take the form of a difference calculation with respect to predetermined absolute dose values.

Returning to FIG. 4, if the exit image evaluation at 424 indicates that the absolute dose at any point in the CIAO exceeds the total dose, a determination of an error based on overdose is made at 426 and an error signal can be generated at 416. As noted above, the error signal may result in automatic shut-off of the radiation field at 418 and/or notification to the radiation system operator of the error at 420. The evaluation at 424 can be repeated (via 422) until the irradiation for the field is complete.

Once the field is determined to be complete at 428, the radiation beam is turned off at 430. Subsequently, full portal dosimetry can be performed at 432, which can involve, for example, difference and gamma processing (see also 506 in FIG. 5) to produce a full 2-D analysis of the measured exit dose, in absolute dose values. If the 2-D analysis reveals that the dose delivered to the patient is non-compliant at 434, a determination of an error based on overdose or underdose is made at 436 and an error signal can be generated at 438. For example, if the analysis values exceed pre-defined action levels with respect to a predetermined absolute dose map (e.g., a percentage over or under the desired cumulative dose at that particular point of the EPID), then a determination of non-compliance can be made and an error signal generated. As noted above, the error signal may result in notification to the radiation system operator of the error at 420. Alternatively or additionally, the error signal at 438 can produce an interlock at 440 that prevents further irradiation fields, which interlock can be overridden by an operator to continue treatment.

If the 2-D analysis reveals that the dose delivered to the patient is compliant at 434, it is determined if additional radiation fields are desired at 442. However, if the analysis reveals that an underdose was delivered, additional radiation fields can be determined to deliver the desired dose. If no further fields are needed, the treatment terminates at 444. Otherwise, the process can repeat by returning to 406 to configure the patient and the radiation system for the next radiation field.

Figure 6:
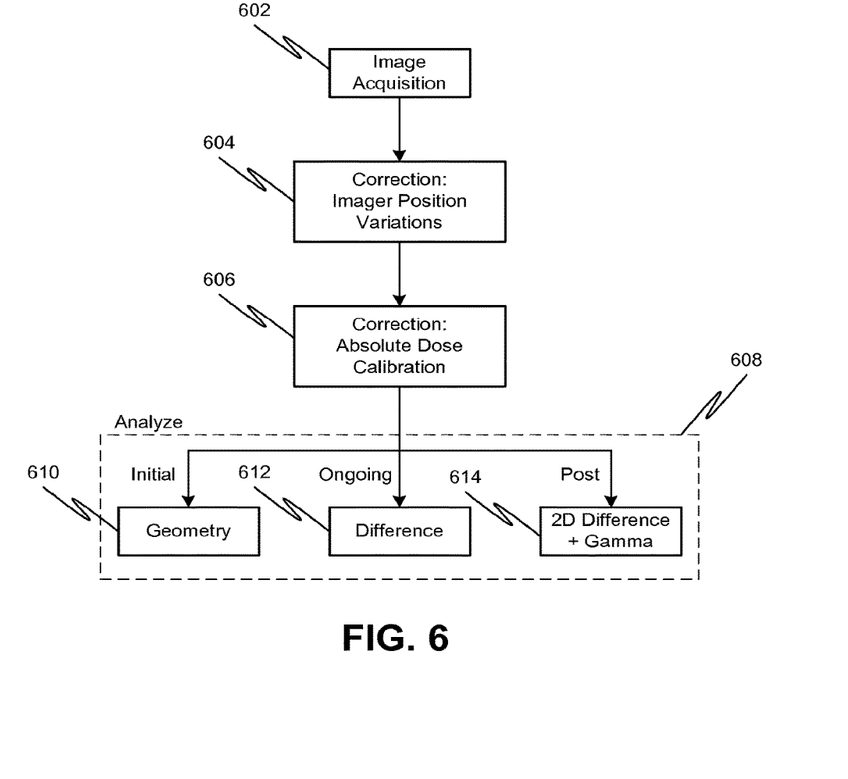
FIG. 6 shows exemplary aspects of image processing associated with dose verification during and after treatment, according to various embodiments of the disclosed subject matter.

FIG. 6 is a diagram summarizing aspects of the image acquisition and processing for dose verification. Image frames obtained by the EPID are acquired (602), which are then corrected for EPID position variations (604). The image frames are then processed to produce an exit image, which is further processed to yield absolute dose values (606) based on calibration of the EPID. The absolute dose values can be used for various analyses (608) during and after irradiation. For example, the absolute dose measurements are used during an initial time period after the start of treatment to confirm compliance of the irradiation beam with the desired CIAO (610). The absolute dose measurements acquired can also be used to provide an ongoing verification that the absolute dose received by the patient does not exceed a planned total dose for the field, for example, by a difference calculation (612). After irradiation, a more comprehensive analysis of the absolute dose values and/or EPID exit images can be performed to determine 2-D compliance of the irradiation with a pre-treatment plan. Thus, a 2-D difference and gamma calculations can be performed (614).

Although not illustrated in FIG. 6, the geometry (610) and difference (612) calculations can be combined such that both checks, or alternating checks, are performed at the beginning of treatment and periodically during treatment. For example, instead of just an initial geometry check and subsequent overdose checks, the initial check may include other checks in addition to the geometry check while subsequent periodic checks can include other checks in place of or in addition to the overdose check. The process flow diagram of FIG. 7 reflects such an embodiment.

Figure 7:
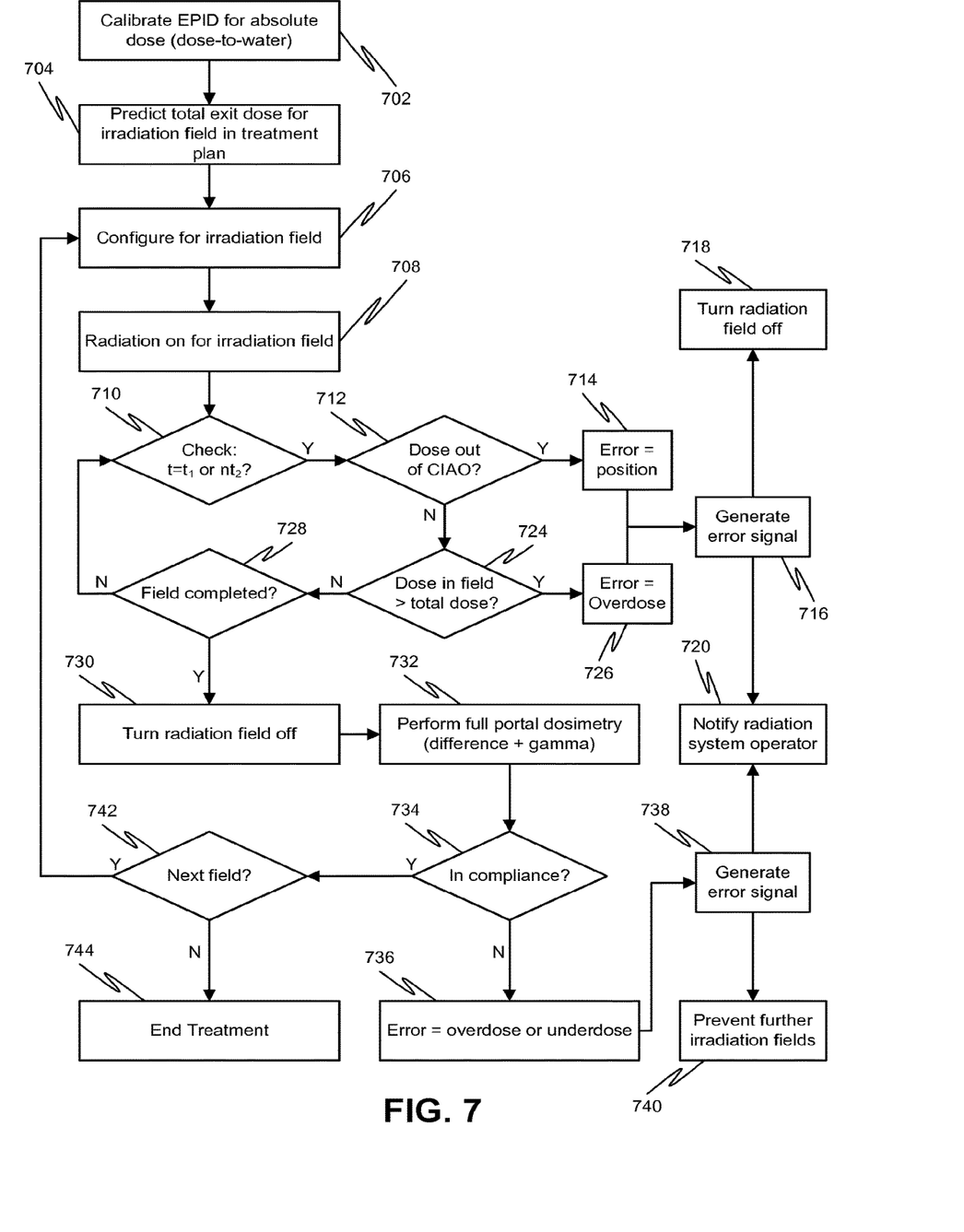
FIG. 7 is a process flow diagram of a dose verification method with both geometry and overdose checks, according to various embodiments of the disclosed subject matter.

Referring to FIG. 7, a process flow diagram of another exemplary dosimetric verification method is shown. At 702, the EPID is calibrated to provide absolute dose measurements (dose-to-water) of the radiation at the EPID based on exit images obtained during irradiation of the patient. Calibration to provide absolute dose measurements can be performed as described in the incorporated by reference October 2007 publication noted above. At 704, a treatment plan can be generated that predicts the absolute dose values at the EPID for each irradiation field. The geometry of the CIAO and the total absolute dose (i.e., the maximum cumulative dose for the irradiation field) are noted for dose verification during the irradiation.

At 706, the system can be configured for a particular irradiation field. For example, the patient can be positioned on the treatment couch. The EPID can then be extended and positioned with respect to the patient in order to detect exit image frames, i.e., to detect radiation from the radiation system that has passed through the patient. The radiation system can then be configured for a particular irradiation field, for example, by positioning the MLC or beam limiting components to provide a desired CIAO.

After configuration for the irradiation field is complete, the radiation beam is turned on at 708. An initial check of the irradiation field can be performed at 710. For example, at one second after the initiation of irradiation (i.e., when $t=t_1=1$ s), it is determined at 712 if the applied irradiation field complies with the desired CIAO for the field. If the exit image analysis indicates that a dose is received outside of the CIAO, a determination of an error based on position or geometry is made at 714 and an error signal can be generated at 716. The error signal may result in automatic shut-off of the radiation field at 718 and/or notification to the radiation system operator of the error at 720. The notification to the radiation system operator at 720 can be in the form of a general error indication (e.g., visual or audio alarm, or on-screen pop-up notification, that an error exists), a specific error indication (e.g., description of the nature of the error), or a graphical error indication (e.g., a graphical representation on an exit image obtained by the EPID).

Subsequently or concurrently, an evaluation of the cumulative absolute dose received at the EPID with respect to the predicted total dose for the irradiation field is performed at 724. If the exit image evaluation at 724 indicates that the absolute dose at any point in the CIAO exceeds the total dose, a determination of an error based on overdose is made at 726 and an error signal can be generated at 716. As noted above, the error signal may result in automatic shut-off of the radiation field at 718 and/or notification to the radiation system operator of the error at 720.

If the dose is determined to be compliant with both the desired CIAO at 712 and total dose at 724, irradiation can continue subject to periodic compliance evaluation (i.e., the geometry check at 712 and the total dose at 724). Such an evaluation may be performed periodically or continuously. For example, the evaluation of exit images for geometry and total dose compliance may occur at discrete periodic time periods to reduce the amount of processing involved without substantially increasing the risk of injury to the patient, for example, every five seconds after the initiation of irradiation (i.e., when $t=n \times t_2 = n \times 5$ s) as determined at 710. However, other time periods, either shorter or longer, for the ongoing evaluation are also possible according to one or more contemplated embodiments.

Figure 8:
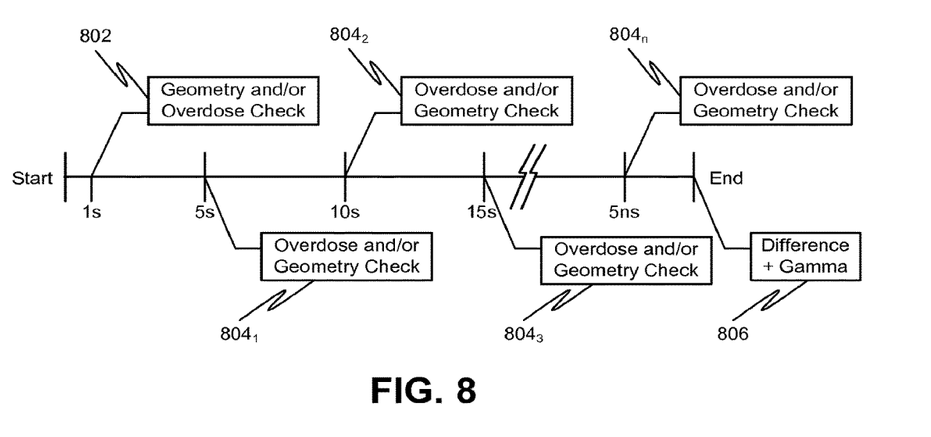
FIG. 8 shows exemplary timing of combined quality assurance checks during and after treatment, according to various embodiments of the disclosed subject matter.

FIG. 8 shows an exemplary time line for different dose verification analyses. For example, one second after initiation of irradiation for a particular field, a geometry check 802 that compares the irradiation field to the desired CIAO is performed (i.e., 712 in FIG. 7). The initial check 802 can also include an overdose check (i.e., 724 in FIG. 7). If no errors are indicated or irradiation continues, then an ongoing check $804_n$ can be performed at five second intervals after initiation of irradiation for the particular field. For example, each ongoing check $804_n$ can include an overdose check (i.e., 724 in FIG. 7) and a geometry check (i.e., 712 in FIG. 7). Alternatively, the ongoing checks $804_n$ can alternate between the overdose check and the geometry check. For example, ongoing check $804_1$ can be an overdose check, ongoing check $804_2$ can be a geometry check, ongoing check $804_3$ can be another overdose check, and so on.

If no errors are indicated or irradiation continues after the first ongoing check $804_1$, a second check $804_2$ can be performed at ten seconds, a third overdose check $804_3$ can be performed at fifteen seconds, and additional overdose checks $804_n$ can be performed at each five second interval (i.e., 5n) until irradiation terminates. Such time periods for the geometry and overdose checks are merely exemplary and other time periods are also contemplated. The geometry and/or overdose checks can take the form of a difference calculation with respect to predetermined absolute dose values at the EPID.

Returning to FIG. 7, once the field is determined to be complete at 728, the radiation beam is turned off at 730. Subsequently, full portal dosimetry can be performed at 732, which can involve, for example, difference and gamma processing (see also 806 in FIG. 8) to produce a full 2-D analysis of the measured exit dose, in absolute dose values. If the 2-D analysis reveals that the dose delivered to the patient is non-compliant at 734, a determination of an error based on overdose or underdose is made at 736 and an error signal can be generated at 738. For example, if the analysis values exceed pre-defined action levels with respect to a predetermined absolute dose map (e.g., a percentage over or under the desired cumulative dose at that particular point of the EPID), then a determination of non-compliance can be made and an error signal generated. As noted above, the error signal may result in notification to the radiation system operator of the error at 720. Alternatively or additionally, the error signal at 738 can produce an interlock at 740 that prevents further irradiation fields, which interlock can be overridden by an operator to continue treatment.

If the 2-D analysis reveals that the dose delivered to the patient is compliant at 734, it is determined if additional radiation fields are desired at 742. If no further fields are needed, the treatment terminates at 744. Otherwise, the process can repeat by returning to 706 to configure the patient and the radiation system for the next radiation field.

In embodiments, predictions for the absolute dose at the EPID for the total field are employed. Predictions for individual treatment frames are not needed, thereby reducing the computational resources that may otherwise be required. In addition, synchronization of the prediction with the treatment, i.e., based on the MLC shape, is not necessary since the prediction employed is for the total field and not individual frames. Thus, the above-described embodiments can be applicable to any radiation treatment type, not just IMRT treatments.

Although embodiments have been described where simplified comparisons of absolute dose measurements are performed during irradiation to reduce the amount of processing power and time required, more complex comparisons can also be performed during irradiation according to one or more contemplated embodiments. For example, instead of calibrating the EPID and processing images to yield absolute dose values, the pre-treatment calculations can predict the radiation image in the amorphous silicon of the EPID after having passed through the patient. The process flow diagram of FIG. 9 reflects such an embodiment.

Figure 9:
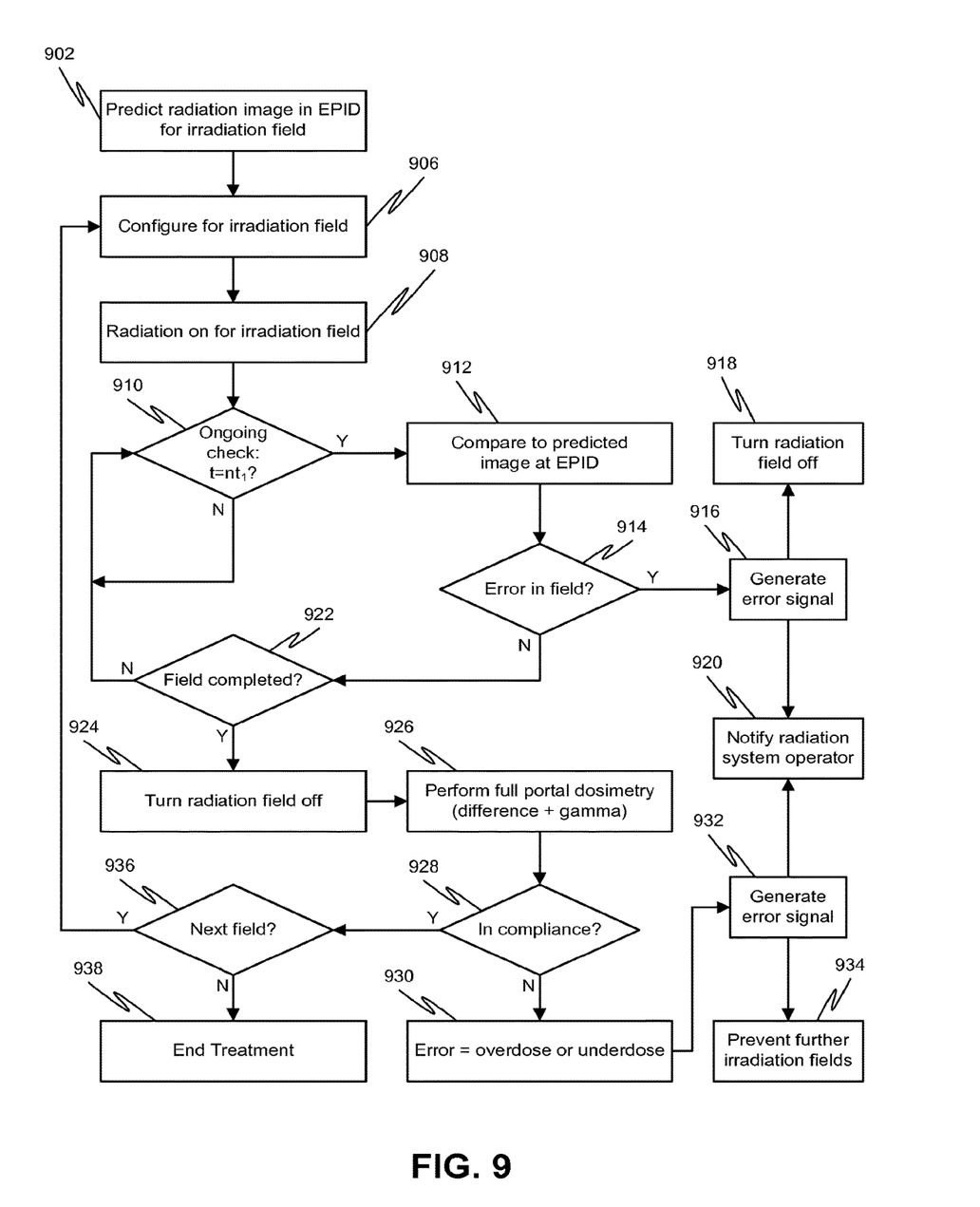
FIG. 9 is a process flow diagram of another dose verification method, according to various embodiments of the disclosed subject matter.

At 902, a treatment plan is generated that predicts the exit dose in the amorphous silicon of the EPID after the radiation has passed through the patient. At 906, the system can be configured for a particular irradiation field. For example, the patient can be positioned on the treatment couch. The EPID can then be extended and positioned with respect to the patient in order to detect exit image frames, i.e., to detect radiation from the radiation system that has passed through the patient. The radiation system can then be configured for a particular irradiation field, for example, by positioning the MLC or beam steering components to provide a desired CIAO.

After configuration for the irradiation field is complete, the radiation beam is turned on at 908. An ongoing evaluation for compliance with the desired dose profile can be performed. Such an evaluation may be performed periodically (e.g., every five seconds) or continuously. Processing of the image frames for determination of compliance may be configured to occur in real-time or near-real time (e.g., less than one second). However, the evaluation of the images may occur at discrete time periods to reduce the amount of processing involved without substantially increasing the risk of injury to the patient. For example, every second after the initiation of irradiation (i.e., when $t=n \times t_1 = n \times 1$ s) as determined at 910, a comparison of the radiation image in the amorphous silicon of the EPID to the predicted radiation image for the irradiation field can be made at 912. Such a comparison can include, but is not limited to, a full portal dosimetry analysis, e.g., including difference and/or gamma processing, as time will allow.

If the comparison at 912 indicates that the dose is not compliant (e.g., due to overdose, underdose, or dose outside of CIAO) at 914, an error signal can be generated at 916. The error signal may result in automatic shut-off of the radiation field at 918 and/or notification to the radiation system operator of the error at 920. The notification to the radiation system operator at 920 can be in the form of a general error indication (e.g., visual or audio alarm, or on-screen pop-up notification, that an error exists), a specific error indication (e.g., description of the nature of the error), or a graphical error indication (e.g., a graphical representation on an exit image obtained by the EPID).

Once the field is determined to be complete at 922, the radiation beam is turned off at 924. Optionally, full portal dosimetry can be performed at 926, which can involve difference and gamma processing to produce a full 2-D analysis of the measured images. If the 2-D analysis reveals that the radiation images are non-compliant at 928, a determination of an error based on overdose or underdose is made at 930 and an error signal can be generated at 932. For example, if the values exceed pre-defined action levels with respect to a predetermined dose map (e.g., a percentage over or under the desired cumulative dose at that particular point of the EPID), then a determination of non-compliance can be made and an error signal generated. As noted above, the error signal may result in notification to the radiation system operator of the error at 920. Alternatively or additionally, the error signal at 932 can produce an interlock at 934 that prevents further irradiation fields, which interlock can be overridden by an operator to continue treatment.

If the 2-D analysis reveals that the radiation images are compliant at 928, it is determined if additional radiation fields are desired at 936. If no further fields are needed, the treatment terminates at 938. Otherwise, the process can repeat by returning to 906 to configure the patient and the radiation system for the next radiation field.

In one or more embodiments of the disclosed subject matter, methods for verifying radiation dose received by a patient from a radiation therapy system are provided. The methods can include irradiating a field using a radiation beam from the radiation therapy system. The methods can also include, during the irradiating, acquiring a continuous stream of image frames from an EPID (i.e., a cine stream) that is arranged to detect radiation exiting the patient. The methods can further include, during the irradiating, processing the stream of image frames in real-time to obtain absolute dose measurements at the EPID in the field as dose-to-water values, and determining compliance with pre-determined characteristics for the field by comparing the processed images with the predetermined characteristics. The methods can additionally include generating an error signal in response to a determination of non-compliance based on the comparing.

In one or more embodiments of the disclosed subject matter, the continuous stream of EPID images can be MV images. In one or more embodiments of the disclosed subject matter, the EPID can include backscatter shielding.

In one or more embodiments of the disclosed subject matter, the EPID does not have backscatter shielding and the processing includes correcting the EPID images for backscatter. In one or more embodiments of the disclosed subject matter, the predetermined characteristics can include a predicted total dose in the field after the full treatment, and the comparing can be a difference comparison between the absolute dose measurement and the predicted total dose. In one or more embodiments of the disclosed subject matter, a determination of non-compliance based on overdose can be made in response to an absolute dose measurement exceeding the predicted total dose. In one or more embodiments of the disclosed subject matter, the determining compliance can be repeated at regular intervals after initiation of the irradiating, for example, at regular intervals no more than five seconds apart.

In one or more embodiments of the disclosed subject matter, the predetermined characteristics can include a CIAO of the field, and the comparing can be a geometric comparison between the absolute dose measurements and the CIAO. In one or more embodiments of the disclosed subject matter, a determination of non-compliance based on positioning can be made in response to an absolute dose measurement being outside the CIAO. In one or more embodiments of the disclosed subject matter, the determining compliance can be performed within one second after initiation of the irradiating.

In one or more embodiments of the disclosed subject matter, a time from the processing of images to the generating an error signal does not exceed one second. In one or more embodiments of the disclosed subject matter, the error signal can be an alert to an operator of the radiation therapy system. In one or more embodiments of the disclosed subject matter, the error signal can be a shutoff signal to the radiation therapy system which turns off the radiation beam.

In one or more embodiments of the disclosed subject matter, the methods can include, after the irradiating, further analyzing the acquired EPID images by performing at least one of a 2-D dose difference analysis and a gamma analysis. In one or more embodiments of the disclosed subject matter, a second error signal can be generated in response to a determination of at least one of an underdose, overdose, or dose outside of CIAO based on the further analyzing. In one or more embodiments of the disclosed subject matter, the second error signal can be an alert to an operator of the radiation therapy system or an interlock that prevents further irradiation using the radiation therapy system.

In one or more embodiments of the disclosed subject matter, the methods can include, prior to the irradiating, predicting the total exit dose image, in absolute dose-to-water, for the field. In one or more embodiments of the disclosed subject matter, a graphical representation of the noncompliance can be displayed on one of the EPID images.

In one or more embodiments of the disclosed subject matter, systems can include a real-time verification device configured to receive a continuous stream of exit image frames (i.e., cine stream) and to process in real-time the continuous stream of image frames so as to obtain absolute dose measurements at an imaging device in a field of a radiation therapy as dose-to-water values. In one or more embodiments of the disclosed subject matter, the verification device can be configured to analyze the dose measurements with respect to predetermined characteristics for the field and to generate an error signal if the dose measurements are not compliant with one or more of the predetermined characteristics.

In one or more embodiments of the disclosed subject matter, systems can include an EPID as the imaging device, the EPID being configured to generate said continuous stream of images by detecting radiation exiting a patient. In one or more embodiments of the disclosed subject matter, the EPID can include backscatter shielding. In one or more embodiments of the disclosed subject matter, the EPID has no backscatter shielding and the system is configured to correct EPID images for backscatter.

In one or more embodiments of the disclosed subject matter, systems can include a radiation therapy device or system with a source that generates a radiation beam for irradiating the patient in performing the radiation therapy. In one or more embodiments of the disclosed subject matter, the verification device can be configured to analyze the dose measurements during irradiation of the patient. In one or more embodiments of the disclosed subject matter, the radiation therapy device or system can be configured to cease irradiation in response to said error signal.

In one or more embodiments of the disclosed subject matter, systems can include a memory for storage of the processed continuous stream of image frames and for storage of a total exit dose image or value. In one or more embodiments of the disclosed subject matter, systems can include a display device operatively coupled to the verification device and configured to display a graphical representation of non-compliance on an exit dose image.

In one or more embodiments of the disclosed subject matter, a portal dosimetry module can be configured to analyze one of the exit images by performing at least one of a 2-D dose difference analysis and a gamma analysis.

In one or more embodiments of the disclosed subject matter, non-transitory computer-readable storage media and a computer processing systems can be provided. In one or more embodiments of the disclosed subject matter, non-transitory computer-readable storage media can be embodied with a sequence of programmed instructions for verifying radiation dose received at an EPID from a radiation therapy system, the sequence of programmed instructions embodied on the computer-readable storage medium causing the computer processing systems to perform one or more of the disclosed methods.

It will be appreciated that the modules, processes, systems, and devices described above can be implemented in hardware, hardware programmed by software, software instruction stored on a non-transitory computer readable medium or a combination of the above. For example, a method for radiation dose verification can be implemented, for example, using a processor configured to execute a sequence of programmed instructions stored on a non-transitory computer readable medium. For example, the processor can include, but is not limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and devices can be implemented as a single processor or as a distributed processor. Further, it should be appreciated that the steps mentioned herein may be performed on a single or distributed processor (single and/or multi-core). Also, the processes, modules, and sub-modules described in the various figures of and for embodiments herein may be distributed across multiple computers or systems or may be co-located in a single processor or system. Exemplary structural embodiment alternatives suitable for implementing the modules, sections, systems, means, or processes described herein are provided below.

The modules, processes, systems, and devices described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the methods, processes, modules, devices, and systems (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the methods, systems, or a computer program products (software program stored on a non-transitory computer readable medium).

Furthermore, embodiments of the disclosed methods, processes, modules, devices, systems, and computer program product may be readily implemented, fully or partially, in software using, for example, object or object-oriented software development environments that provide portable source code that can be used on a variety of computer platforms. Alternatively, embodiments of the disclosed methods, processes, modules, devices, systems, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the methods, processes, modules, devices, systems, and computer program product can be implemented in hardware and/or software using any known or later developed systems or structures, devices and/or software by those of ordinary skill in the applicable art from the function description provided herein and with a general basic knowledge of radiation therapy systems, control systems, and/or computer programming arts.

Features of the disclosed embodiments may be combined, rearranged, omitted, etc., within the scope of the invention to produce additional embodiments. Furthermore, certain features may sometimes be used to advantage without a corresponding use of other features.

It is thus apparent that there is provided in accordance with the present disclosure, system, methods, and devices for radiation dose verification. Many alternatives, modifications, and variations are enabled by the present disclosure. While specific embodiments have been shown and described in detail to illustrate the application of the principles of the present invention, it will be understood that the invention may be embodied otherwise without departing from such principles. Accordingly, Applicants intend to embrace all such alternatives, modifications, equivalents, and variations that are within the spirit and scope of the present invention.

The invention claimed is:

1. A method for verifying radiation dose received by a patient from a radiation therapy system, the method comprising:
irradiating a field using a radiation beam from the radiation therapy system;
acquiring a stream of image frames from an electronic portal imaging device (EPID) that is arranged to detect radiation exiting the patient;
processing the stream of image frames in real-time to obtain dose measurements at the EPID in the field;
determining compliance with predetermined characteristics for the field by comparing the processed image frames with the predetermined characteristics; and
generating an error signal in response to a determination of non-compliance based on the comparing.

2. The method of claim 1, wherein the determining comprises an initial determination of compliance followed by a plurality of subsequent determinations.

3. The method of claim 2, wherein the initial determination of compliance comprises determining whether the irradiation field complies with a desired complete irradiation area outline (CIAO) for the field.

4. The method of claim 3, wherein upon the determination that the irradiation field does not comply with the desired complete irradiation area outline (CIAO) for the field, an error signal is generated to indicate that the received radiation dose is outside of the (CIAO).

5. The method of claim 4, wherein the error signal comprises a visual and/or audio and/or on-screen pop-up signal to notify a system operator of the error.

6. The method of claim 5, further comprising notifying the system operator of the nature of the error.

7. The method of claim 4, wherein upon the determination that the field does not comply with the desired complete irradiation area outline (CIAO) for the field, the irradiation is automatically shut-off.

8. The method of claim 6, further comprising graphically representing the error.

9. The method of claim 4, further comprising determining the source of error and rectifying the error.

10. The method of claim 9, wherein the source of error comprises one or more of a missing and/or damaged multileaf collimator (MLC), missing and/or damaged radiation field shaping element of the radiation therapy system, mispositioned patient, mispositioned gantry, and mispositioned EPID, and the rectifying comprises one or more of replacing and/or fixing the missing multileaf collimator (MLC), replacing and/or repositioning the field shaping element, repositioning the patient by moving a patient couch, repositioning the gantry, and repositioning the EPID.

11. The method of claim 2, wherein the initial determination occurs at a first time interval after starting irradiation, and the subsequent determinations occur at regular or irregular time intervals after starting irradiation.

12. The method of claim 2, wherein the initial and subsequent determinations occur simultaneously or sequentially.

13. The method of claim 12, wherein the subsequent determinations include one or more determinations made during irradiation of the patient and a final determination made post patient irradiation.

14. The method of claim 13, wherein the one or more determinations comprise determining whether the radiation dose received by the patient exceeds a planned dose for a particular field.

15. The method of claim 13, wherein the one or more determinations comprise determining whether the cumulative dose received by the patient exceeds a total planned dose for a particular field.

16. The method of claim 14, wherein upon a determination that the radiation dose exceeds a planned dose, an error signal is generated.

17. The method of claim 16, wherein the error signal comprises a visual and/or audio and/or on-screen pop-up signal to notify a system operator of the error.

18. The method of claim 17, further comprising notifying the system operator of the nature of the error.

19. The method of claim 18, further comprising graphically representing the error.

20. The method of claim 14, wherein upon the determination that the radiation dose exceeds a planned dose, the irradiation is automatically shut-off.

21. The method of claim 14, further comprising determining the source of error and rectifying the error.

22. The method of claim 14, wherein the source of error comprises one or more of a stuck multileaf collimator (MLC), an issue with a radiation beam steering element, and rectifying includes fixing the stuck multilieaf collimator (MLC), and solving the beam steering problem prior to further irradiation.

23. The method of claim 14, wherein the determination further comprises determining whether a condition of underdose or overdose is present at different points in the CIAO.

24. The method of claim 23, wherein upon a determination of an overdose condition, an error signal is generated so as to notify an operator of the overdose condition.

25. The method of claim 23, wherein upon a determination of an overdose condition, an interlock condition is asserted to automatically prevent proceeding to the next irradiation field.

26. The method of claim 13, wherein the final determination includes a 2D analysis of the dose delivered to the patient.

27. The method of claim 26, wherein upon a determination that the dose delivered to the patient is under or over a predetermined percentage of a desired cumulative dose map, an error signal is generated and sent to an operator.

28. The method of claim 27, wherein if the dose delivered to the patient is under the predetermined percentage of a desired cumulative dose map, the operator determines whether additional radiation fields are needed.

29. The method of claim 1, wherein the dose measurements at the EPID in the field are dose-to-water values.

* * * * *